United States Patent [19]

Carse

[11] Patent Number: 4,480,998

[45] Date of Patent: Nov. 6, 1984

[54] DENTAL PINNING DEVICE

[76] Inventor: Murray D. Carse, 6 Queensway Ct., Hatfield, Hertfordshire AL10 ONR, England

[21] Appl. No.: 419,298

[22] Filed: Sep. 17, 1982

[30] Foreign Application Priority Data

Sep. 24, 1981 [GB] United Kingdom ............... 8128961

[51] Int. Cl.³ ............................................... A61C 5/04
[52] U.S. Cl. .................................................. 433/225
[58] Field of Search .................... 433/174, 211, 225

[56] References Cited

U.S. PATENT DOCUMENTS

| | | | |
|---|---|---|---|
| 3,740,851 | 6/1973 | Weissman | 433/225 |
| 4,060,896 | 12/1977 | Wahnish | 433/174 |
| 4,187,611 | 2/1980 | Chan | 433/225 |
| 4,219,620 | 8/1980 | Carse | 433/225 |
| 4,365,958 | 12/1982 | Vlock | 433/225 |

FOREIGN PATENT DOCUMENTS 1313168 11/1962 France .
 604673 9/1978 Switzerland .
2016631 9/1979 United Kingdom .

*Primary Examiner*—Gene Mancene
*Assistant Examiner*—David L. Tarnoff
*Attorney, Agent, or Firm*—Flynn, Thiel, Boutell & Tanis

[57] ABSTRACT

A dental pinning device comprises a shank having at one end a formation for engagement with a latching-type dental handpiece and carrying at the other end, by way of a shearing neck, a threaded pin for screwing into a tooth, wherein the threaded pin is part of a metal end-piece which also includes an integral shaft of smaller diameter projecting from the pin and the shank and shearing neck are formed as a body of synthetic resin material and are attached to the end piece by moulding of the synthetic resin material around the shaft.

5 Claims, 2 Drawing Figures

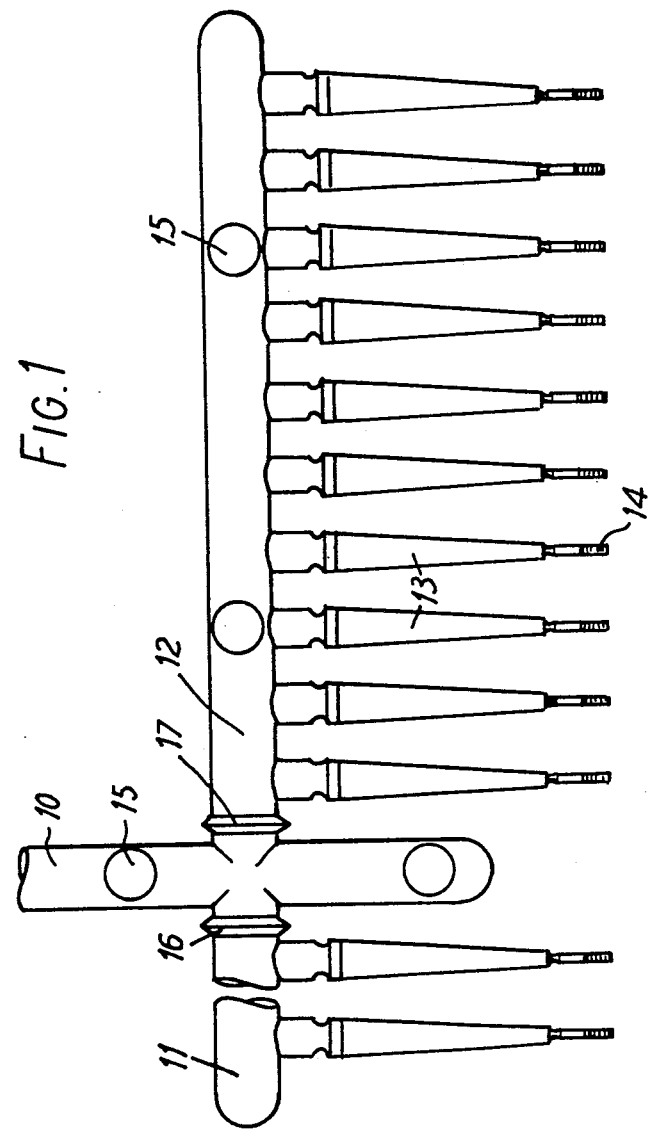

DENTAL PINNING DEVICE

The present invention relates to dental pinning devices which are used to insert pins into the structure of a broken or worn down tooth to receive a restoration or superstructure. The invention is particularly concerned with self-threading pins which are screwed into a pre-drilled hole in the tooth.

Various pinning devices have been described and are in use for insertion of a self-threading pin to act as an anchor for a restoration. In particular U.K. Patent Specification No. 1,482,681 describes a pinning device which comprises a shank of which one end is provided with a flat and a part-annular groove for engagement in conventional manner with a latching-type dental hand-piece. The pin is formed integrally with the metal shank and is connected to the other end of the shank by a narrow neck. When the pin is screwed into the tooth and bottoms in the pre-drilled hole, continued rotation of the shank causes shearing of the neck and leaves the pin projecting from the tooth. This is thus a self-shearing pin. An improved form of integral pinning device which enables the pin to align itself in the pre-drilled hole is described in my U.K. Patent Specification No. 1,597,483 (corresponding to my U.S. Pat. No. 4,219,620).

There is also available on the market the Whaledent "Linkpin" dental pinning device in which the shank is moulded from a synthetic resin material and has at one end the flat and part-annular groove for latching into a hand-piece. The threaded pin is part of a metal portion which includes the shearing neck and has a spigot which is fitted into a bore in the end of the shank.

In this case, as in all the other known devices, when the threaded pin has been screwed into the tooth and has sheared off from the shank at the neck there is left projecting from the tooth a metal anchorage member which forms the foundation for the restoration. Whatever materials are used this frequently means that the anchorage member is visible through the restoration.

In accordance with the present invention there is provided a dental pinning device comprising a shank having at one end a formation for engagement with a latching-type dental handpiece and carrying at the other end, by way of a shearing neck, a threaded pin for screwing into a tooth, wherein the threaded pin is part of a metal end-piece which also includes an integral shaft of smaller diameter projecting from the pin and the shank and shearing neck are formed as a body of synthetic resin material and are attached to the end piece by moulding of the synthetic resin material around the shaft.

The shaft, with its coating of synthetic resin material, remains attached to the threaded pin when the neck shears and forms an anchor section projecting from the tooth, the threaded pin being buried within the tooth. Thus no metal parts are exposed and the coating can be of an optically dense material of suitable colour to completely conceal the presence of the metal pin and shaft. The quantity of metal required is so small that it is possible to use gold or other precious metal without excessive cost.

The presence of the coating may also be used to control the shearing action since engagement of the end of the coating with the surface of the tooth will increase the torque acting and produce shearing of the pin, thus replacing the usual engagement of the pin with the bottom of the hole and preventing over-insertion of the pin. This assumes, as will normally be the case, that the coating has an outside diameter greater than that of the thread of the pin.

To ensure a good bond between the metal end-piece and the synthetic resin material, the shaft can be knurled or pitted and may be of non-cylindrical shape. The end-piece can be mounted in a mould and the synthetic resin material cast around the shaft while the body is being formed. In the preferred method of manufacture a plurality of pinning devices are formed simultaneously in a single mould in which the shanks extend laterally from two supporting branches which extend in alignment with each other from opposite sides of a central stem. The branches can be removed from the stem and supplied to the dentist who then separates a pinning device from one of the branches whenever he requires one.

The invention will now be described in more detail with the aid of an example illustrated in the accompanying drawings, in which FIG. 1 is a view of an injection moulding comprising a multiplicity of pinning devices in accordance with the invention, and FIG. 2 is a detail, partially in section, of the end of a single pinning device which carries the threaded pin.

The moulding shown in FIG. 1 comprises a stem 10 with two opposite branches 11 and 12 aligned with one another. Each of the branches 11 and 12 has ten pinning devices 13 projecting laterally from one side of the branch. Each pinning device 13 is complete with a metal end-piece 14 which is incorporated into the moulding as will be described in more detail below. The branches 11 and 12 and the stem 10 have bosses 15 which serve for ejection of the moulding from the mould. The branches 11 and 12 can be broken from the stem 10 at the junctions 16 and 17, respectively.

Each of the pinning devices 13 has a tapering shank composed of synthetic resin material. Reference may be made to U.K. Patent Specification No. 1,597,483 (corresponding to U.S. Pat. No. 4,219,620) for details of the shape of the shank, including the flat and part-annular groove for attachment to a dental hand-piece. The present shank differs only in the material of which it is made. At the other end of the shank is a narrow neck 18, shown in FIG. 2, which is also composed of synthetic resin material and forms the shear point for the pinning device.

As seen in FIG. 2, the end-piece 14 consists of a threaded pin 19 and an integral shaft 20 of smaller diameter. Before the end-piece 14 is placed in the mould, the surface of the shaft 20 is pitted to enable the synthetic resin to key onto it. During the moulding operation in which the shank and neck are formed there is also formed a coating or sleeve 21 over the shaft 20 which secures the end piece 14 to the shaft. The coating or sleeve 21 may be of slightly larger diameter than the threads of the pin 19. Thus the screwing of the pin 19 into a pre-drilled hole in the tooth is terminated by abutment of the sleeve 21 against the tooth followed by shearing of the neck 18 due to the increased torque. The anchor section left projecting from the tooth is thus entirely covered by the synthetic resin material which may be chosen to conceal the metallic end piece while providing a good bond with the restoration. For the latter purpose it is evident that various different shapes may be used.

I claim:

1. A dental pinning device comprising a shank having at one end a formation for engagement with a latching-type dental handpiece and carrying at the other end, by way of a shearing neck, a threaded pin for screwing into a tooth, wherein the threaded pin is part of a metal end-piece which also includes an integral shaft of smaller diameter projecting from the pin and the shank and shearing neck are formed as a body of synthetic resin material and are attached to the end piece by moulding of the synthetic resin material around the shaft.

2. A device as claimed in claim 1 in which the synthetic resin material moulded around the shaft has an outside diameter greater than that of the thread of the pin.

3. A device as claimed in claim 1 in which the shaft has a roughened surface to key the synthetic resin material to the shaft.

4. A device as claimed in claim 1 in which the shank is of noncylindrical shape.

5. A dental pinning device comprising:

a metal endpiece including a threaded pin for screwing from one end thereof into a tooth and and an integral shaft of diameter smaller than said threaded pin and projecting from the other end of the threaded pin; and a synthetic resin body including a shank, a formation at one end of said shank for engagement with a latching type dental handpiece, a shearing neck at the other end of the shank, and an end portion connected to said other end of said shank by said shearing neck, said end portion of said synthetic resin body being moulded around and thereby fixed to said shaft of said metal endpiece, such that said metal endpiece is attached to said synthetic resin body, said metal threaded pin extending from said synthetic resin body for screwing into a tooth by rotational driving through said synthetic resin body, said synthetic resin shearing neck being breakable by excessive rotational driving torque to leave said synthetic resin end portion exposed on said tooth and fixed thereon by said metal threaded pin screwed into said tooth.

* * * * *